(12) United States Patent
Holm et al.

(10) Patent No.: US 6,264,636 B1
(45) Date of Patent: Jul. 24, 2001

(54) FLUSHING DEVICE

(75) Inventors: Hans Henrik Holm; Jacob Holm, both of Hellerup (DK); Niels Chr. Holm, London (GB)

(73) Assignee: Maersk Medical A/S (DK)

( * ) Notice: Subject to any disclaimer, the term of this patent is extended or adjusted under 35 U.S.C. 154(b) by 0 days.

(21) Appl. No.: 09/077,497
(22) PCT Filed: Dec. 2, 1996
(86) PCT No.: PCT/DK96/00501
  § 371 Date: May 29, 1998
  § 102(e) Date: May 29, 1998
(87) PCT Pub. No.: WO97/20583
  PCT Pub. Date: Jun. 12, 1997

(30) Foreign Application Priority Data

Dec. 1, 1995 (DK) .................................................. 1361/95

(51) Int. Cl.⁷ ................................................... A61M 5/178
(52) U.S. Cl. ........................................... 604/183; 600/156
(58) Field of Search ........................... 604/26–30, 36–37, 604/183, 186; 600/156, 159; 210/136

(56) References Cited

U.S. PATENT DOCUMENTS

| 1,925,230 | 9/1933 | Buckhout . |
| 3,892,226 | 7/1975 | Rosen . |
| 4,282,873 | 8/1981 | Roth . |
| 4,880,408 | 11/1989 | Cumes et al. . |

FOREIGN PATENT DOCUMENTS

2 592 584   1/1986  (FR) .

*Primary Examiner*—Sharon Kennedy
*Assistant Examiner*—Kevin C. Sirmons
(74) *Attorney, Agent, or Firm*—Brinks Hofer Gilson & Lione (57) ABSTRACT

A device for use in the flushing of a bodily cavity includes a container (1,2) provided with a first connection opening for a pump/suction means 13) and a second connection opening for a tube connection communicating, in a situation of use of the device, with the bodily cavity to be flushed, a tube member (7) extending inwards into the container (1,2) from the second connection opening, said tube member (7) being formed with at least one first opening (8) through which flushing liquid is pumped by the pump/suction means (13) and with at least one second opening through which flushing liquid is sucked out of the cavity to the interior of the container. A one-way valve (11) is provided at the second opening to admit and block flow into the container (1,2) through said opening, and a filter element is arranged between the second opening and the connection opening of the pump/suction means.

12 Claims, 6 Drawing Sheets

FLUSHING DEVICE

The invention relates to a device for use in the flushing of a bodily cavity and comprising a container provided with a first connection opening for a pump/suction means and with a second connection opening for a tube connection communicating, in a situation of use of the device, with the bodily cavity to be flushed, a tube member extending inwards into the container from the second connection opening, said tube member being formed with at least one first opening through which flushing liquid is pumped by the pump/suction means and with at least one second opening through which flushing liquid is sucked out of the cavity into the interior of the container, means being provided at the second opening to allow and block flow into the container through said opening.

Such devices are used e.g. in connection with treatments where tissue pieces have been scraped or cut off from the surrounding tissue. The treatment may e.g. involve prostatic surgery in which such tissue pieces are scraped or cut off using endoscopy equipment known per se.

After scraping, the tissue pieces will be present in the bodily cavity, which, in case of prostatic surgery, is the urinary bladder and the urinary tracts, In such cases, to remove these tissue pieces, a device of the type mentioned in the opening paragraph is mounted post-operatively on the endoscopic tube, which is still inserted in the urinary tracts. Liquid is hereby pumped inwards through the tube and into the urinary bladder and is sucked again, causing the scraped or cut tissue pieces to be flushed out.

A large number of such devices is known. However, all of these are vitiated by drawbacks to a greater or smaller degree, which make their use a time-consuming operation, and the achieved result is not always satisfactory.

The most commonly used device of this type today (the so-called Ellik evacuator) comprises a container with an opening for a pump/suction means and an opening which can communicate with an endoscopic tube through a hose connection. The openings in the container are not shielded against each other, and the sucked tissue pieces are therefore collected in the container exclusively by their gravitational precipitation. This known and commonly used device involves a great risk of tissue pieces being pumped into the bodily cavity again, and also a risk of tissue pieces being sucked into the pump suction means. The necessary gravitational precipitation makes the use of this system time-consuming and inefficient. Since the sucked tissue pieces are moreover to transported to a laboratory for analysis, these must be removed from the container and be transferred to a transport container. This adds to the time consumption. The handling of the tissue pieces moreover involves a considerable risk of infection.

U.S. Pat. No. 4,880,408 discloses a device of the type defined in the opening paragraph. This device involves the risk that the sucked tissue pieces will find their way to the pump/suction means and hide there. This is of considerable importance for the further analysis of the removed tissue pieces. The device of this US patent is moreover vitiated by the same drawbacks with respect to transport as are described in connection with the above-mentioned Ellik evacuator.

Accordingly, the object of the present invention is to provide a device of the type mentioned in the opening paragraph which contributes to rapid and efficient flushing to a significantly greater degree than the known devices, and where the tissue pieces after flushing are present in the container itself.

This object is achieved according to the invention by a device of the type mentioned in the opening paragraph, which is characterized in that a filter element is disposed around the second opening so as to separate the second opening from the connection opening of the pump/suction means.

When the device is constructed in this manner, it is ensured that the flushed tissue pieces do not settle in the pump/suction means itself, since these will be retained by the filter element in any event and thus be present in the container itself.

Advantageously, the device of the invention consists of a container body and a container lid, said first and second openings being provided in the container lid, said tube element forming part of the lid, and said filter element being formed by a detachable apertured plate. This results in a simple structure in terms of manufacture, as it just consists of three parts. A one-way valve (non-return valve) or optionally a flap element is expediently provided in connection with the closable second opening.

The first opening or openings in the tube element are expediently provided as axially directed slots in the part of the tube element facing the filter element. This results in a simple structure in terms of manufacture, and the provision of the slots at the end of the tube element adjoining the filter element moreover ensures that there will just be a small dead volume in the tube element.

The device may include a transport lid capable of replacing the container lid. This is expedient, as the scraped tissue pieces, usually after the completion of surgery, are to be transported for further analysis at a laboratory. In this connection, the container will usually be filled with a preservation liquid in the form of formalin, which is to be poured off again prior to the analysis at the laboratory. Here, the filter element again serves as a sieve, causing the scraped tissue pieces to be retained in the container when formalin liquid is poured off. Accordingly, the resulting structure, when being handled, involves a smaller risk of infection than is the case with the previously known devices.

The device of the invention is expediently made of a transparent material as far as the container body and the container lid are concerned. This allows monitoring of the flushing of the tissue pieces, while monitoring e.g. whether bleedings occur from the site of surgery.

The pump/suction means used in connection with the device is expediently a squeezable bulb capable of expanding again by its own spring force. In principle, however, it is possible to use other types of pump/suction means.

The invention will be explained more fully below with reference to the accompanying drawing, in which.

Figure 1:
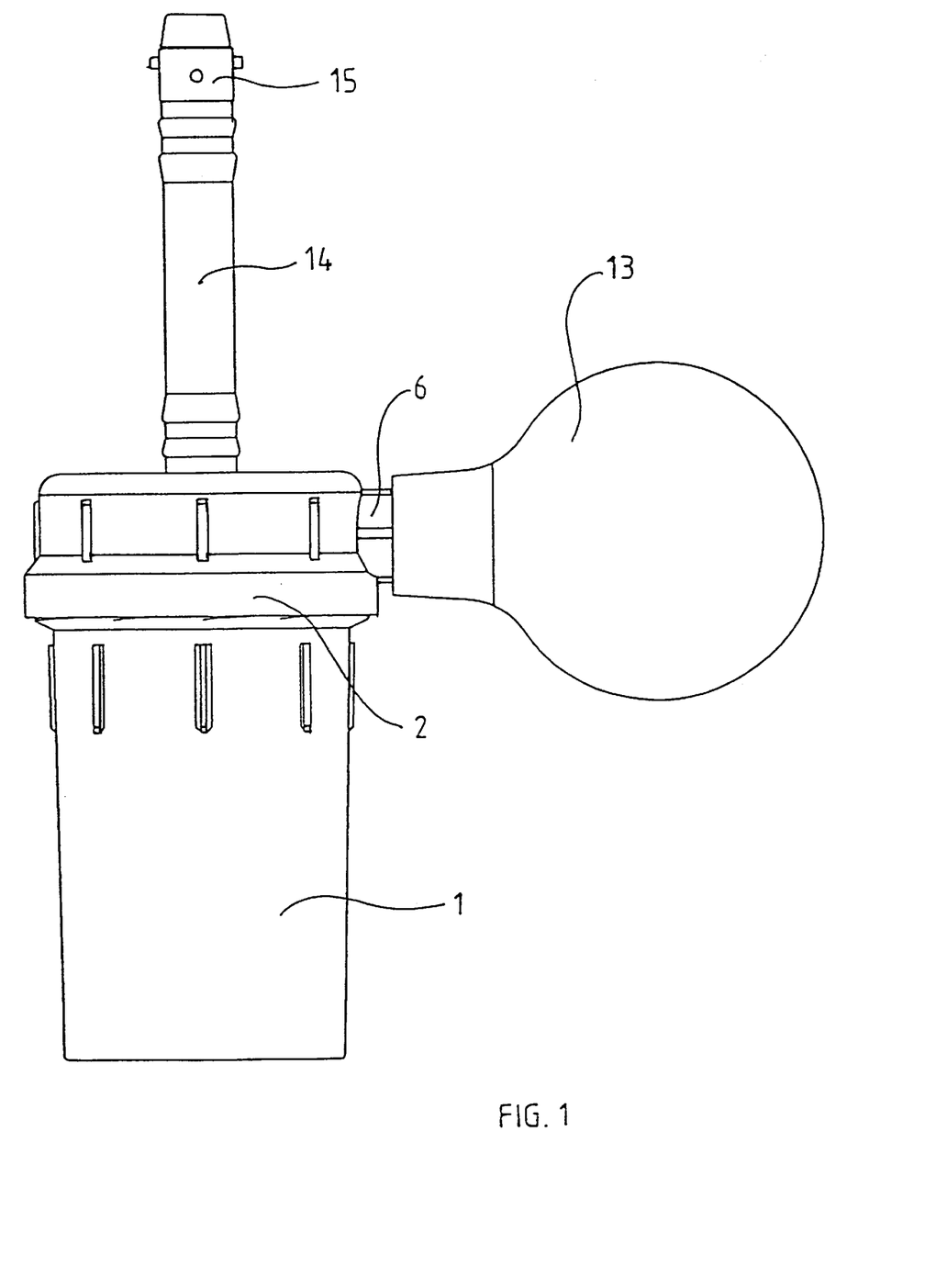
FIG. 1 is a lateral view of a device of the invention.

It appears from FIG. 1, which is a lateral view of a device of the invention, that this device comprises a container body 1 on which a lid 2 is mounted. The lid 2 comprises a tube connection 6 connecting a pump/suction means 13 in the form of a bulb with interior of the device. An additional opening in the lid connects a tube connection 14 having a connector 15, which parts 14, 15 are to provide the connection to e.g. an endoscopic tube inserted into the urinary tracts.

Figure 2:
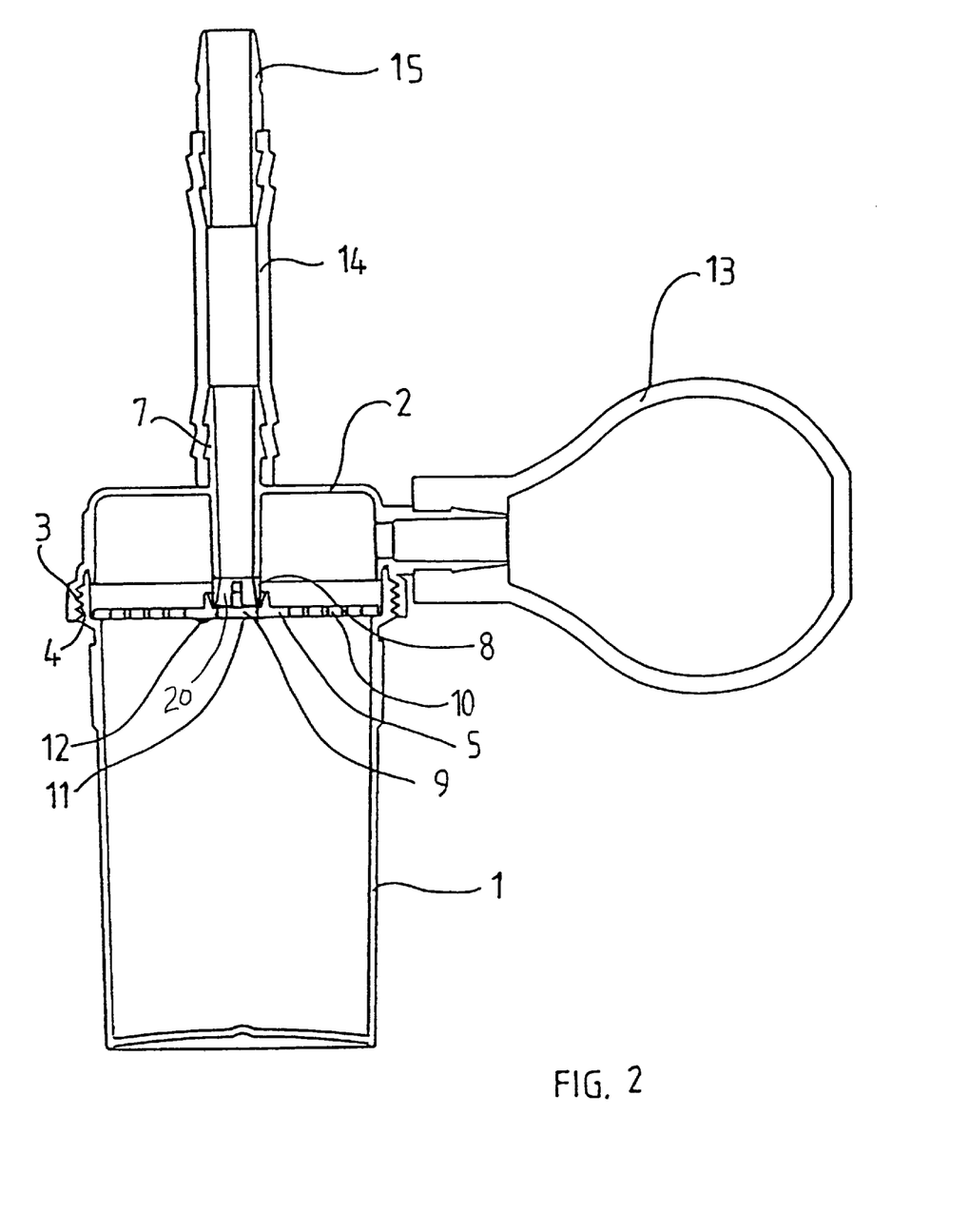
FIG. 2 is a vertical sectional view of the device shown in FIG. 1.

FIG. 2, which is a sectional view of the device shown in FIG. 1, likewise shows the container body 1, the lid 2 with the tube connection 6 and the pump/suction means 13. It is moreover apparent that the lid is formed with a tube connection 7 which communicates with the tube 14 and the connector 15 and comprises a first opening 8. The container body and the lid are mutually secured by means of cooperating threaded parts 3, 4. The container accommodates an apertured plate 5 which serves as a filter element for flushed tissue pieces. The apertured plate 5 comprises a central aperture 9 which communicates with second opening 20 in the tube element 7 in the container lid. A plurality of smaller apertures 10 is provided around the central aperture. These apertures are shown more clearly in FIGS. 3–5. A non-return valve 11 (NRV) is arranged in connection with the central aperture on the side facing the interior of the container body. This non-return valve is secured by means of two pins 12 which are heat-deformed around holes in the non-return valve.

Figure 3:
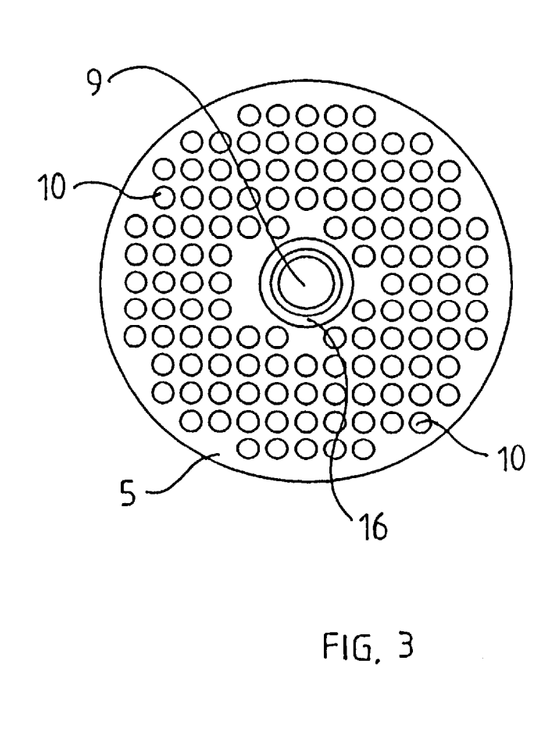
FIG. 3 is a vertical sectional view of the device shown in FIG. 1.
Figure 4:
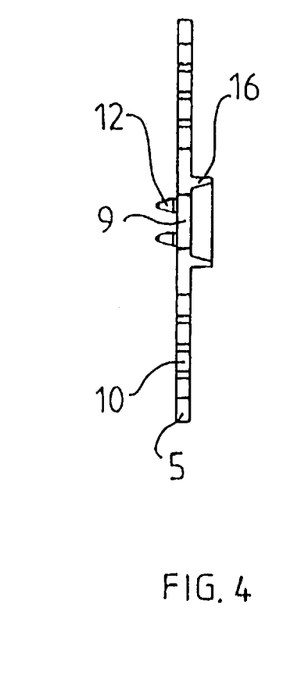
FIG. 4 is a sectional view of the filter element shown in FIG. 3.
Figure 5:
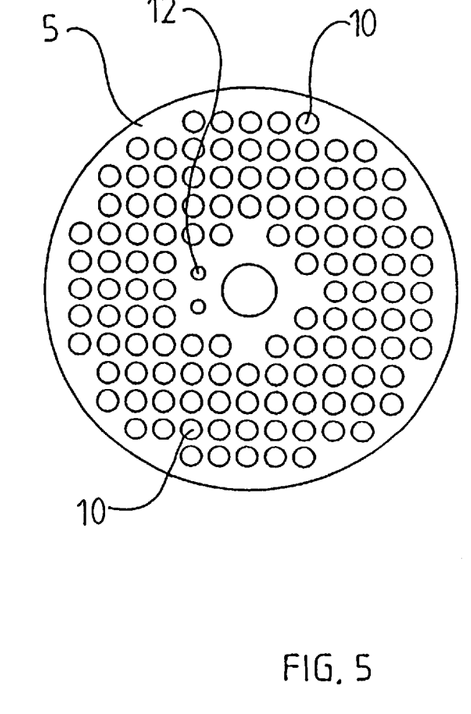
FIG. 5 is a bottom view of the filter element shown in FIGS. 3 and 4.

FIGS. 3, 4 and 5, which are top, lateral sectional and bottom views of the filter element 5, shows the central aperture 9, the smaller apertures 10 positioned around it, and a flange part 16 serving to receive the tube element 7. Two holes are provided at the side of the central aperture 9 to receive the pins 12, which secure the non-return valve after heat deformation.

Figure 6:
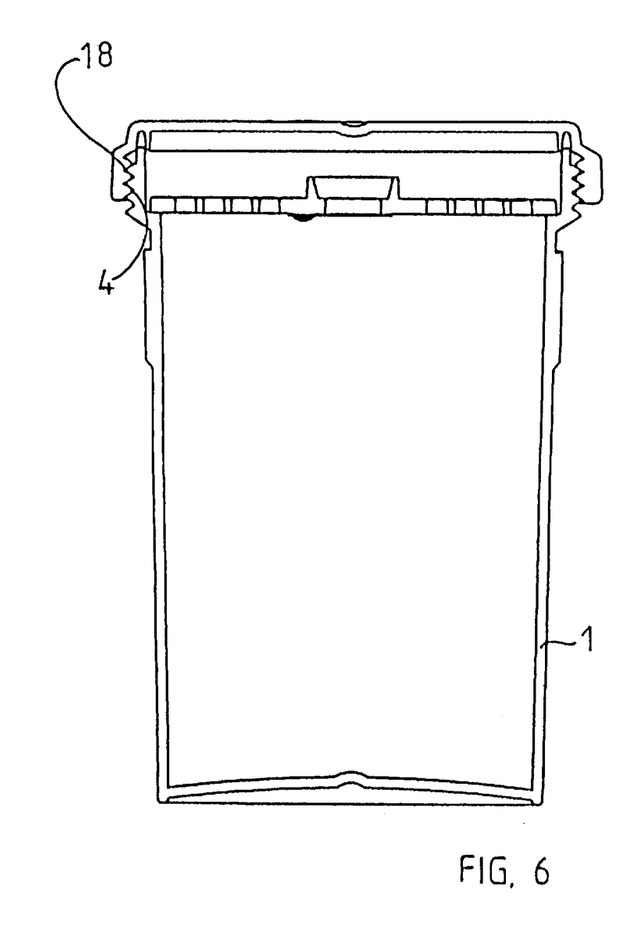
FIG. 6 is a sectional view of the container associated with a device of the invention with a transport lid mounted thereon, said filter element being still present in the container.
Figure 7:
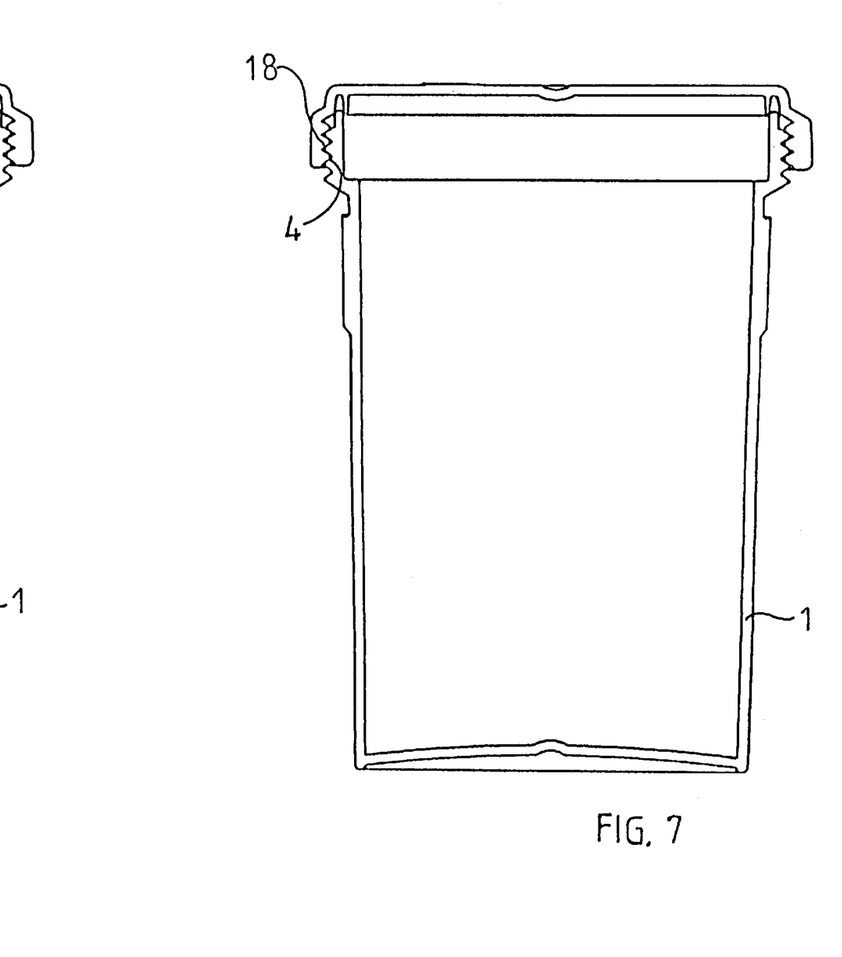
FIG. 7 shows the container shown in FIG. 6 without inserted filter element in the container.

FIGS. 6 and 7 show a container body 1 in section, where the lid part 2 has been removed and replaced by a transport lid 18. FIG. 6 shows the container with transport lid, said container accommodating a filter element, and FIG. 7 shows the corresponding container without a filter element.

Figure 8:
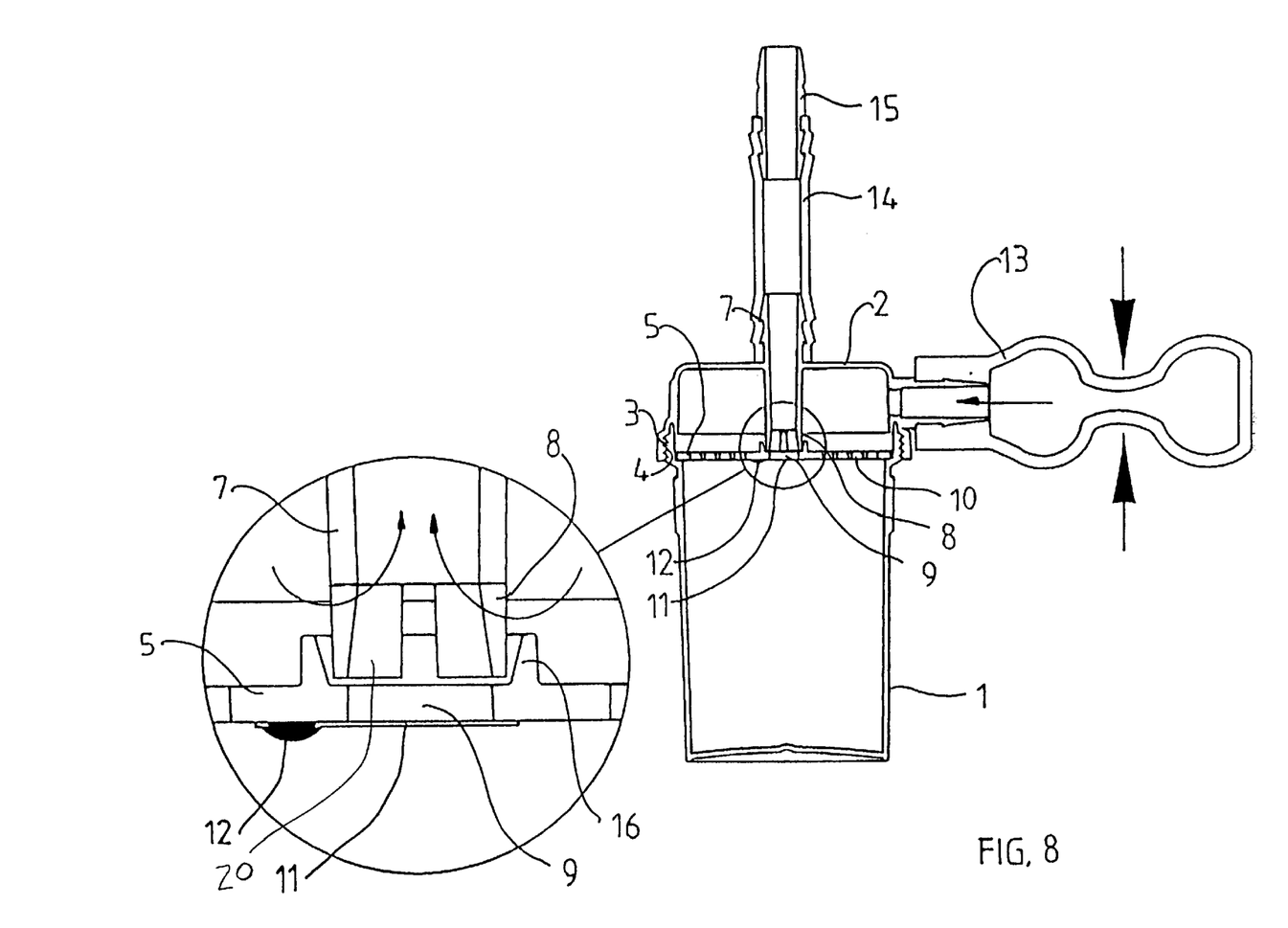
FIG. 8 shows the flow paths of the liquid upon compression of a pump/suction means belonging to the device of the invention.

FIG. 8 shows the flow paths of the liquid present in the device on compression of the pump/suction bulb 13. Compression of bulb drives the liquid through the tube connection 6 and further through the slots 8 into the tube element 7 and further through the tube connection 14 and the connector 15 into the bodily cavity to be flushed. Because of the pressure impact which propagates through the liquid through the apertures 10 in the filter element, the non-return valve will be kept closed by compression of the pump/suction bulb.

Figure 9:
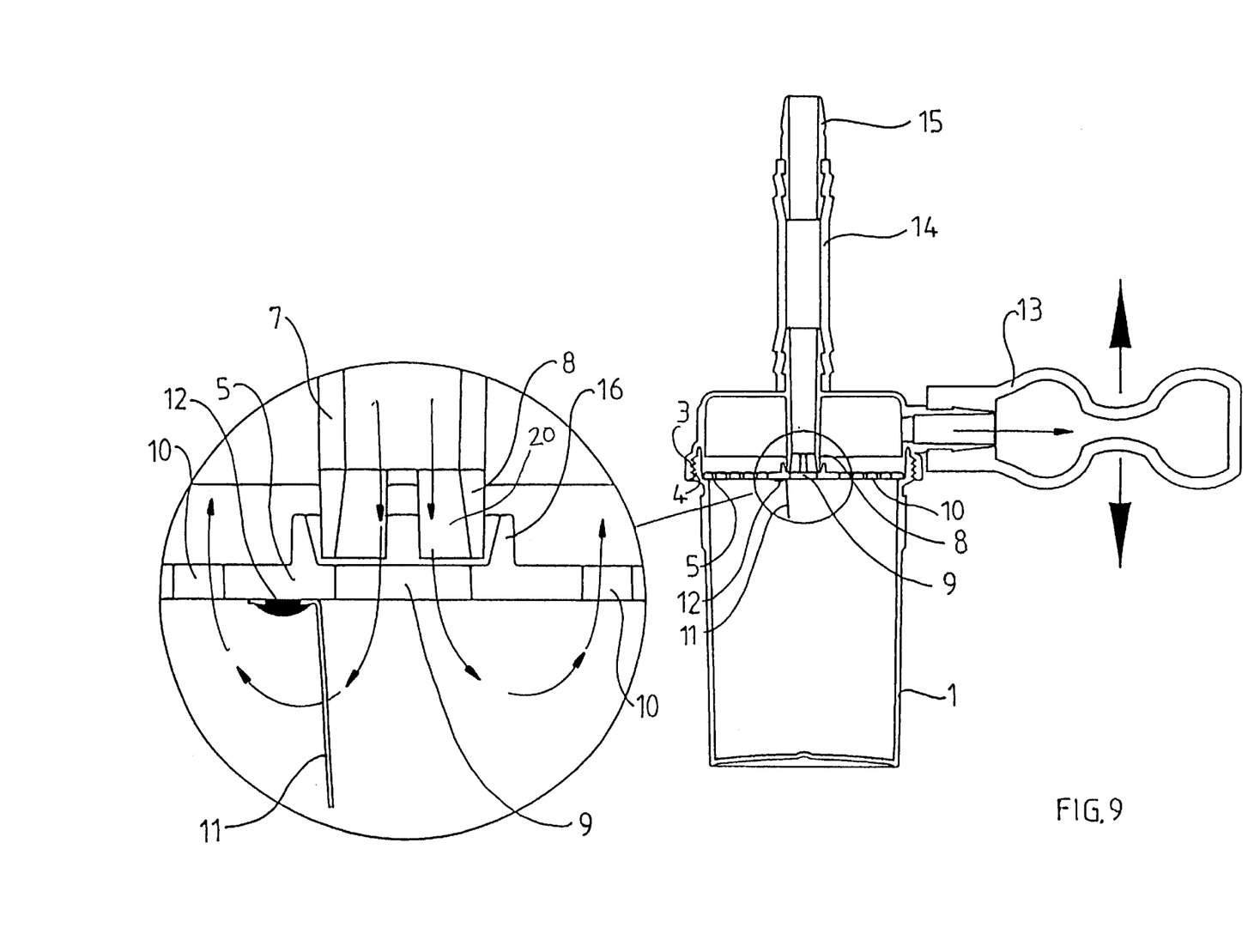
FIG. 9 shows the flow paths in a device of the invention upon expansion of the pump/suction means.

On expansion of the pump/suction bulb, as shown in FIG. 9, the liquid flow path will be through the central aperture 9 in the filter element and from there via the holes 10 in the apertured plate back to the suction pump bulb. The sucked tissue pieces will hereby be retained by the filter element 5 and thus remain in the container 1. It is clear in this connection that the provision of the these flow conditions is a dimensioning of the various hole sizes with respect to each other so that a correct proportion between the flow resistances through these is achieved.

As shown in FIG. 8, the filter element 5 divides the container into first and second regions. The first region is disposed above the filter element 5, and the second region is disposed below the filter element 5. Flushing liquid that is sucked out of the body cavity enters the second region via the central aperture 9, and flushing liquid passing to and from the bulb 13 flows through the first region.

Also as shown in FIG. 8, the slots 8 are axially directed in a portion of the tube element 7 facing the filter element 5.

What is claimed is:

1. A device for use in flushing a bodily cavity, said device comprising a container provided with a first connection opening for a pump/suction means and a second connection opening for a tube connection communicating, in a situation of use of the device, with the bodily cavity to be flushed, a tube member extending inwards into the container from the second connection opening, said tube member comprising a first opening through which flushing liquid is pumped by the pump/suction means and a second opening through which flushing liquid is sucked out of the bodily cavity to the interior of the container, a one-way valve being provided at the second opening to admit flow into the container through said second opening, and a filter element mounted in the container, said filter element positioned such that the second opening is on a first side of the filter element, and both the first opening and the first connection opening for the pump/suction means are on a second side of the filter element;

said filter element dividing the container into first and second regions, said second opening directing flushing liquid that is sucked out of the bodily cavity into said second region, said first connection opening directing flushing liquid pumped by the pump/suction means through the first region into the first opening.

2. A device according to claim 1, wherein the container comprises a container body and a container lid, said first and second connection openings being provided in the lid.

3. A device according to claim 2 wherein the lid and the tube member are formed in one piece.

4. A device according to claim 2 or 3, further comprising a transport lid configured to replace the lid provided with the first and second openings.

5. A device for use in flushing a bodily cavity, said device comprising a container provided with a first connection opening for a pump/suction means and a second connection opening for a tube connection communicating, in a situation of use of the device, with the bodily cavity to be flushed, a tube member extending inwards into the container from the second connection opening, said tube member comprising a first opening through which flushing liquid is pumped by the pump/suction means and a second opening through which flushing liquid is sucked out of the bodily cavity to the interior of the container, a one-way valve being provided at the second opening to admit flow into the container through said second opening, and a filter element mounted in the container, said filter element positioned such that the second opening is on a first side of the filter element, and both the first opening and the first connection opening for the pump/suction means are on a second side of the filter element, said filter element comprising a detachable apertured plate having a passage which, in an assembled state of the device, is present in alignment with the second opening of the tube member.

6. A device according to claim 5, wherein the first opening in the tube member comprises at least one axially directed slot in a portion of the tube member.

7. A device according to claim 1, wherein the one-way valve comprises a flap element.

8. A device according to claim 1, wherein the pump/suction means comprising a squeezable bulb operative to expand again by its own spring force.

9. A device according to claim 1, wherein the container comprises a transparent material.

10. A device for use in flushing a bodily cavity, said device comprising a container provided with a first connection opening for a pump/suction means and a second connection opening for a tube connection communicating, in a situation of use of the device, with the bodily cavity to be flushed, a tube member extending inwards into the container from the second connection opening, said tube member comprising at least one first opening through which flushing liquid is pumped by the pump/suction means and a second opening through which flushing liquid is sucked out of the bodily cavity to the interior of the container, a one-way valve being provided at the second opening to admit flow into the container through said second opening, wherein     a filter element is arranged between the second opening and the first connection opening for the pump/suction means, and wherein     the filter element comprises a detachable apertured plate having a passage which, in an assemble state of the device, is present in alignment with the second opening of the tube member.

11. A device of claim 10 wherein the filter element divides the container into first and second regions, said second opening directing flushing liquid that is sucked out of the bodily cavity into said second region, said first connection opening directing flushing liquid pumped by the pump/suction means through the first region into the first opening.

12. A device for use in flushing a bodily cavity, said device comprising a container provided with a first connection opening for a pump/suction means and a second connection openings for a tube connection communicating, in a situation of use of the device, with the bodily cavity to be flushed, a tube member extending inwards into the container from the second connection opening, said tube member comprising a first opening through which flushing liquid is pumped by the pump/suction means and a second opening through which flushing liquid is sucked out of the bodily cavity to the interior of the container, a one-way valve being provided at the second opening to admit flow into the container through said second opening, and a filter element mounted in the container, said filter element positioned such that the second opening is on a first side of the filter element, and both the first opening and the first connection opening for the pump/suction means are on a second side of the filter element; said filter element cooperating with the container to define a collection region on a first side of the filter element, said second opening directing flushing liquid that is sucked out of the bodily cavity into said collection region; said filter element positioned such that flushing liquid in the collection region passes through the filter element before reaching the first connection opening and before reaching the first opening.

\* \* \* \* \*

UNITED STATES PATENT AND TRADEMARK OFFICE
CERTIFICATE OF CORRECTION

PATENT NO.    : 6,264,636 B1  Page 1 of 1
DATED         : July 24, 2001
INVENTOR(S)   : Hans Henrik Holm et al.

It is certified that error appears in the above-identified patent and that said Letters Patent is hereby corrected as shown below:

<u>Title page,</u>
Item [57], ABSTRACT,
Delete lines 1 through 16, and substitute the following in its place:
-- A device for use in flushing a body cavity includes a container provided with a first connection opening for a pump/suction device and a second connection opening for a tube connection. This tube connection communicates with the body cavity to be flushed when the device is in use. A tube member extends inwards into the container from the second connection opening. This tube member is formed with at least one first opening through which flushing liquid is pumped by the pump/suction device, and with at least one second opening through which flushing liquid is sucked out of the cavity to the interior of the container. A one-way valve at the second opening admits flow into the container while blocking reverse flow, and a filter element is arranged between the second opening and the connection opening for the pump/suction device. --.

<u>Column 5,</u>
Line 21, delete "A device" and substitute -- The device -- in its place.

Signed and Sealed this

Twenty-sixth Day of November, 2002

Attest:

Attesting Officer

JAMES E. ROGAN
*Director of the United States Patent and Trademark Office*